(12) United States Patent
Eifler

(10) Patent No.: US 9,795,754 B2
(45) Date of Patent: *Oct. 24, 2017

(54) VENTILATOR MASK WITH A FILLER AND METHOD OF PRODUCTION

(71) Applicant: Martin Eifler, Glueckstadt (DE)

(72) Inventor: Martin Eifler, Glueckstadt (DE)

(73) Assignee: Loewenstein Medical Technology S.A., Luxembourg (LU)

( * ) Notice: Subject to any disclaimer, the term of this patent is extended or adjusted under 35 U.S.C. 154(b) by 620 days.

This patent is subject to a terminal disclaimer.

(21) Appl. No.: 14/134,163

(22) Filed: Dec. 19, 2013

(65) Prior Publication Data

US 2014/0123983 A1 May 8, 2014

Related U.S. Application Data

(63) Continuation of application No. 11/999,737, filed on Dec. 6, 2007, now Pat. No. 8,684,004.

(30) Foreign Application Priority Data

Dec. 6, 2006 (DE) .......................... 10 2006 057 798

(51) Int. Cl.
*A61M 16/06* (2006.01)
*A61M 16/08* (2006.01)

(52) U.S. Cl.
CPC ........ *A61M 16/06* (2013.01); *A61M 16/0605* (2014.02); *A61M 16/0616* (2014.02); *A61M 16/0633* (2014.02); *A61M 16/0825* (2014.02)

(58) Field of Classification Search
CPC .............. A61M 15/00; A61M 15/0016; A61M 15/0018; A61M 15/0086; A61M 16/00; A61M 16/0057; A61M 16/0066; A61M 16/0069; A61M 16/04; A61M 16/0434; A61M 16/0488; A61M 16/06; A61M 16/0616; A61M 16/0622; A61M 16/0633; A61M 16/0638; A61M 16/0666; A61M 16/0683; A61M 16/08; A61M 16/0816; A61M 16/10; A61M 16/104; A61M 16/1045; A61M 16/105; A61M 16/1065;
(Continued)

(56) References Cited

U.S. PATENT DOCUMENTS 2,875,757 A * 3/1959 Galleher, Jr. ..... A61M 16/0683
128/206.26
2,931,356 A 4/1960 Schwarz
(Continued)

FOREIGN PATENT DOCUMENTS

DE 4212259 C1 1/1993
DE 10226587 A1 1/2004
(Continued)

*Primary Examiner* — Annette Dixon
(74) *Attorney, Agent, or Firm* — Abel Law Group, LLP

(57) ABSTRACT

Disclosed is ventilator mask comprising an upper part of an elastic material and a mask body, wherein the upper part of the mask is joined with the mask body of the ventilator mask by a mask connection region, wherein a wall of the upper part of the mask bounds at least in certain regions of the wall a cavity which is filled with a filler at least in certain regions of the cavity and the cavity is formed at least in certain regions of the cavity along the periphery of the upper part of the mask.

23 Claims, 8 Drawing Sheets

(58) Field of Classification Search
CPC ............ A61M 16/109; A61M 16/1095; A61M 16/16; A61M 2016/00; A61M 2016/0039; A61M 2016/04; A61M 2016/0409; A61M 2016/0434; A61M 2016/0436; A61M 2016/0438; A61M 2016/0443; A61M 2016/045; A61M 2016/0452; A61M 2016/06; A61M 2016/0605; A61M 2016/0611; A61M 2016/0616; A61M 2016/0627; A61M 2016/0633; A61M 2016/0661; A61M 2205/15; A61M 2205/183; A61M 2205/42; A61M 2209/06; A61M 2210/0618; A62B 18/00; A62B 18/02; A62B 18/025; A62B 18/08; A62B 18/084; A62B 23/00; A62B 23/06; A62B 9/00; A62B 9/02
USPC ............ 128/200.24, 202.23, 202.27, 203.28, 128/203.29, 205.17, 205.23, 205.25, 128/205.27, 206.12, 206.14, 206.19, 128/206.21, 206.23, 206.24, 206.25, 128/206.26, 206.28, 207.11, 848, 857, 128/858, 863, 909, 912
See application file for complete search history.

(56) References Cited

U.S. PATENT DOCUMENTS

| | | | |
|---|---|---|---|
| 3,330,274 A * | 7/1967 | Bennett | A61M 16/06 128/206.26 |
| 3,556,097 A | 1/1971 | Wallace | |
| 3,815,596 A | 6/1974 | Keener et al. | |
| 4,665,570 A | 5/1987 | Davis | |
| 4,755,411 A * | 7/1988 | Wing | A47C 7/18 264/45.1 |
| 4,832,017 A | 5/1989 | Schnoor | |
| 5,222,478 A * | 6/1993 | Scarberry | A61H 31/02 601/44 |
| 5,343,878 A | 9/1994 | Scarberry et al. | |
| 5,429,683 A | 7/1995 | Le Mitouard | |
| 5,592,938 A | 1/1997 | Scarberry et al. | |
| 5,647,357 A * | 7/1997 | Barnett | A61M 16/06 128/205.25 |
| 5,884,624 A | 3/1999 | Barnett et al. | |
| 6,397,847 B1 | 6/2002 | Scarberry et al. | |
| 6,494,206 B1 | 12/2002 | Bergamaschi et al. | |
| 6,631,718 B1 | 10/2003 | Lovell | |
| 6,843,249 B2 | 1/2005 | Bergamaschi et al. | |
| 6,895,965 B2 | 5/2005 | Scarberry et al. | |
| 6,951,218 B2 | 10/2005 | Gradon et al. | |
| 7,743,768 B2 | 6/2010 | Ho et al. | |
| 7,827,990 B1 | 11/2010 | Melidis et al. | |
| 7,870,859 B2 | 1/2011 | Barnett et al. | |
| 8,051,855 B2 | 11/2011 | Ho et al. | |
| 8,371,293 B2 | 2/2013 | Henry et al. | |
| 8,684,004 B2 * | 4/2014 | Eifler | A61M 16/06 128/200.24 |
| 2003/0075181 A1 | 4/2003 | Bergamaschi et al. | |
| 2005/0199239 A1 * | 9/2005 | Lang | A61M 16/06 128/206.24 |
| 2006/0076018 A1 | 4/2006 | Barnett et al. | |
| 2006/0185675 A1 | 8/2006 | Colin | |
| 2007/0107733 A1 | 5/2007 | Ho et al. | |
| 2007/0267017 A1 | 11/2007 | Edwin McAuley et al. | |
| 2008/0006277 A1 | 1/2008 | Worboys et al. | |
| 2008/0032119 A1 | 2/2008 | Feldhahn et al. | |
| 2008/0078386 A1 | 4/2008 | Feldhahn et al. | |
| 2008/0257354 A1 | 10/2008 | Davidson et al. | |
| 2009/0139526 A1 | 6/2009 | Melidis et al. | |
| 2010/0024811 A1 | 2/2010 | Henry et al. | |
| 2010/0282265 A1 | 11/2010 | Melidis et al. | |
| 2011/0088699 A1 * | 4/2011 | Skipper | A61M 16/06 128/206.26 |
| 2013/0112203 A1 | 5/2013 | Henry et al. | |

FOREIGN PATENT DOCUMENTS

| | | |
|---|---|---|
| DE | 102005033650 A1 | 1/2007 |
| DE | 102007042733 A1 | 6/2008 |
| EP | 1099452 A2 | 5/2001 |
| EP | 1116492 A2 | 7/2001 |
| EP | 1900388 A2 | 3/2008 |
| EP | 1982740 A1 | 10/2008 |
| WO | 9300125 A1 | 1/1993 |
| WO | 03105921 A1 | 12/2003 |
| WO | 2005094928 A1 | 10/2005 |
| WO | 2005118040 A1 | 12/2005 |
| WO | 2006024253 A1 | 3/2006 |
| WO | 2007059504 A2 | 5/2007 |
| WO | 2007068044 A1 | 6/2007 |

* cited by examiner

VENTILATOR MASK WITH A FILLER AND METHOD OF PRODUCTION

CROSS-REFERENCE TO RELATED APPLICATIONS

The present application is a continuation of application Ser. No. 11/999,737, filed Dec. 6, 2007, now U.S. Pat. No. 8,684,004, the entire disclosure of which is expressly incorporated by reference herein.

BACKGROUND OF THE INVENTION

1. Field of the Invention

The present invention relates to a ventilator mask.

2. Discussion of Background Information

In medical air supply, patients with a wide variety of respiratory problems are supplied by ventilation systems with air or with oxygen by means of devices that supply the air or an air mixture as a respiratory gas to the nose and/or the mouth. In this regard, the contact interface between the hoses supplying an air mixture and the respiratory openings of the person or other organism (since animals may also sometimes be supplied with respiratory gas) plays an important role.

This interface is usually realized as a ventilator mask that covers only the nose, only the mouth, or both the nose and the mouth, is preferably fastened on the head by flexible straps, and has one or two hose connections. The patient must wear the ventilator mask on his face for hours, overnight, or even for a period of several days, which means that great demands are placed on wearing comfort. Complaints due to pressure points on parts of the face, especially the bridge of the nose, are a burden on the patient. In addition, there is the problem of adjusting the size of the masks to different facial and nasal characteristics of different patients.

To solve both the comfort problem and the size problem, ventilator masks have been developed which comprise a bell-shaped structure that covers the respiratory passages and is adapted to the shape of the face, which can also be referred to as the upper part of the mask or the mask rim, which is made of a flexible material, preferably a skin-compatible silicone, a thermoplastic elastomer (TPE), or polyurethane and is designed to be elastic, and has an inwardly formed peripheral edge that consists of contact lips. The upper part of the mask is intended to serve as the contact surface of the ventilator mask on the face of the patient and thus forms a sealing contact between the ventilator mask and the face.

A gel rim from the prior art is produced from a gel that is enclosed in a protective PU foil. An additional silicone cover lies between the patient's face and the PU gel body. The wall thicknesses of the PU foil and the silicone cover are kept essentially constant.

WO 2005/094928 A1 describes a ventilation device with a ventilator mask, which has a gel rim inserted in the upper part of the mask. The gel rim acts on the lips of the upper part of the mask and thus applies more pressure to parts of the face. This is also intended to provide a better seal in order to allow more precise and economical operation of the air supply system. The gel rim is formed with an essentially uniform thickness. It also has a part that presses against the region of the bridge of the nose. This makes it more difficult to adapt the upper part of the mask to the shape of the parts of the patient's face and makes it necessary to produce parts that are individually shaped for the patient. This makes production more complicated and thus more expensive.

Solutions of this type have the result that a large number of differently shaped mask upper parts must be offered to accommodate faces of different shapes and sizes if one does not wish to make sacrifices with respect to wearing comfort and the level of sealing that can be realized.

SUMMARY OF THE INVENTION

Therefore, the objective of the present invention is to solve the problems described above and to propose an upper part of a ventilator mask that allows optimum exertion of contact pressure on the parts of the face and at the same time allows greater adaptability to different patients with different shapes and sizes of the different parts of their faces, so that a smaller number of different mask sizes is sufficient, and the masks have fewer individual parts. A further objective of the invention is to provide general improvement of the wearing comfort of a ventilator mask and to allow less expensive production.

The objective of the invention is essentially achieved with a mask whose upper part is provided with a cavity that is filled with a filler of a specific consistency and elasticity.

The nature of the filler can be highly varied, from the aforementioned gel materials, such as polyurethane gel, silicone gel or the natural gel agarose, to foamed materials, gas mixtures and liquids, such as, for example, saline solution, which is often used in medicine. Ultimately, it can also be the same material of which the upper part of the mask is made, especially when it is foamed. The integrated construction in accordance with the invention allows the thickness of the walls of the upper part of the mask to be adapted very precisely to requirements to lend greater or lesser stiffness to certain sectors of the upper part of the mask exactly according to requirements.

The invention can be used in nasal and full-face masks, in emergency ventilation, home ventilation and hospital ventilation. The upper part of the mask in accordance with the invention is suitable, for example, for CPAP, APAP, bilevel, and home ventilation. The upper part of the mask in accordance with the invention is suitable for a typical pressure range of the respiratory gas of 0 mbars to 50 mbars.

To produce the upper part of the mask in accordance with the invention, it is proposed that shaping methods be used to produce the upper part of the mask with at least one cavity from an elastic plastic, preferably a silicone or polyurethane, and that this cavity then be filled with the intended filler material. The cavity is preferably filled through at least one hole provided for this purpose. The filling hole is preferably not located in the areas of the upper part of the mask that come into contact with the facial skin.

It is especially preferred for the cavity to be filled by injecting the filling material, and the covering is preferably pierced in the thicker areas of the upper part of the mask. After the filling operation, the one or more filling holes are tightly sealed, especially when the cavity has been filled with liquid or gaseous fillers, for example, with a plug, by welding or by adhesive bonding. Especially gaseous fillers can be pressurized, so that the level of pressure can influence and determine the properties of the upper part of the mask.

In accordance with the invention, the shape, size and local expansion of the filled cavities are selected in such a way that the upper part of the mask develops the most favorable properties. For example, the filled cavity is distributed in such a way in the form of a rim in the wall of the upper part of the mask that it includes either practically the whole wall or only specific sectors of it. The corner region of the upper part of the mask is preferably provided with a local filled rim in order to furnish this region with a desired combination of the properties of elasticity and stiffness.

In refinements of the present invention, it is further proposed that the properties of the filler be varied within the cavity of the invention in the upper part of the mask, according to the site of filling. This makes it possible, by means of local variation of the elasticity and viscosity of the filler, in addition to or alternatively to the varying thickness of the cavity in accordance with the invention, to achieve even better adaptation of the resulting properties of the upper part of the mask that promote wearing comfort to the requirements of use on the face of a patient. The combination of different fillers is likewise part of the specifications of the present invention.

In an alternative method of production, a filler body shaped from an intended filler material is first produced and is then covered with a protective cover by an immersion method or injected in a mold. When gaseous or liquid fillers are used, it can be a shaped bag, which is to be filled and covered with a protective layer.

In accordance with the invention, it is further proposed that, in the area of the bridge of the nose, underlaying the areas of the upper part of the mask that are near the lip with a filler be entirely dispensed with or that the cavity to be filled be made very thin, in order to avoid the generation of too much pressure on the sensitive bridge of the nose. The air seal in the area of the bridge of the nose is preferably produced solely by means of the inwardly formed contact lips, which, due to their high degree of flexibility, also allow greater adaptability to different nose sizes of patients.

It is further proposed that instead of introducing a filler, such as gel or foamed material, into a cavity in the upper part of the mask, it simply be introduced on the inner surface or the outer surface of the walls of the upper part of the mask. This solution offers economic advantages, since the existing dies for the upper parts of masks can continue to be used. To protect the fillers applied in this way to the walls of the upper parts of the mask from soiling or skin contact, their exposed surfaces are then provided with a protective layer. The protective layer is produced either from the filler material that has been melted on or from a third material to be applied. The shape and, in accordance with the invention, the variable thickness of the one or more rim-shaped fillers applied in this way, preferably by spraying or foaming, are realized by a method in which the filler, e.g., in powdered form, emerges from a nozzle and is shaped by different amounts or by different metering or by residence times of different length.

The present invention allows improved adaptation of the compressive forces exerted on the different parts of the face by the upper part of the ventilator mask and a one-part design of the upper part of the mask, which is advantageous for practical use.

It should be noted that the scope of the present invention is not limited solely to the preferred embodiments presented here, but rather extensive combinations and variants of the present invention can be deduced from the independent and dependent claims by an individual with average skill in the art without his having to go beyond the teaching of the present invention.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

DESCRIPTION OF THE PREFERRED EMBODIMENTS

Figure 1:
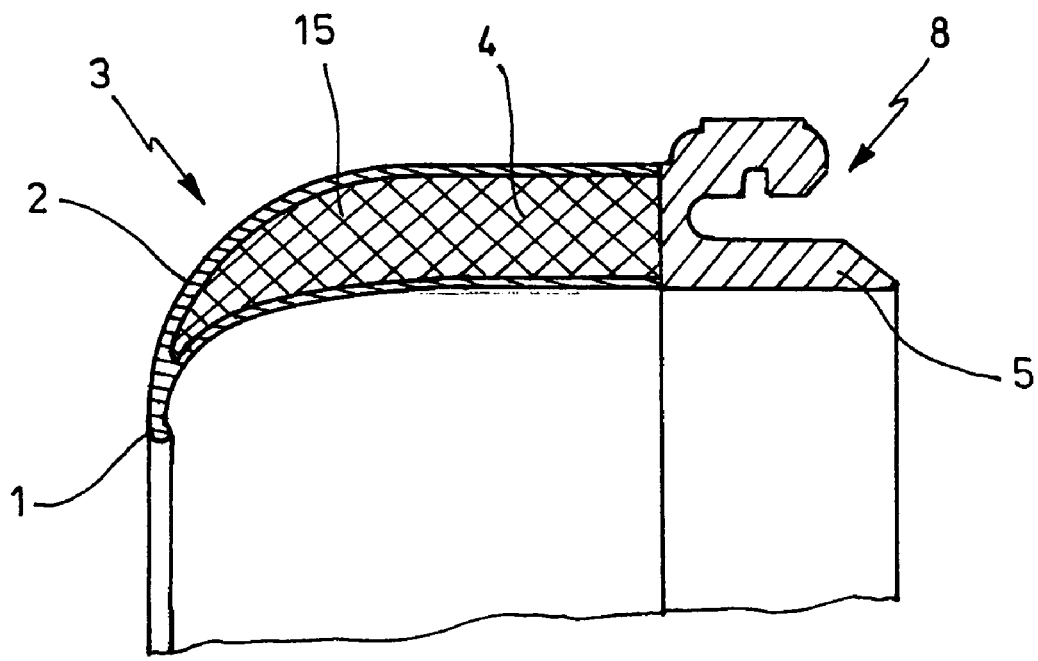
FIG. 1 is a partial sectional view of an embodiment of the upper part of a mask with a cavity and a filler.

FIG. 1 shows a partial section of the upper part 3 of a ventilator mask 8, in whose walls a cavity 4 that is filled with a filler 15 is formed in such a way that the thickness or depth of the filler 15 varies over the cross section of the upper part 3 of the mask. The region of the upper part 3 of the mask that is in contact with the patient is preferably softer.

On its surface intended for contact with different parts of the patient's face, the upper part 3 of the mask terminates in a contact lip 1 that becomes thinner and surrounds the edge to provide the upper part 3 of the mask with a soft and flexible contact zone. The walls of the upper part 3 of the mask terminate in a mask connecting member 5, which is realized either as a single piece with the upper part 3 of the mask and made of the same material or as a separate part that is to be attached by adhesive bonding or welding.

The mask connecting member 5 is mechanically joined with a lower part of the mask (not shown) by means of parts that snap together. Alternatively, it can be undetachably joined with the lower part of the mask by adhesive bonding or welding. The cavity 4 is bounded by an outer skin 2.

In accordance with the invention, the thickness or depth of the filler 15 can also be essentially constant over the cross section of the upper part 3 of the mask.

The upper part 3 of the mask has at least one hole for filling the cavity 4 with a filler 15. This hole is not shown in FIG. 1. It can be located in any desired place in the wall of the upper part 3 of the mask, except in the region of the outer surfaces of the contact lips 1 and the area surrounding this region, since this would cause it to have a disturbing effect on the facial skin with which it would be in contact. The filling hole is preferably sealed with a plug or by adhesive bonding or welding.

Figure 2:
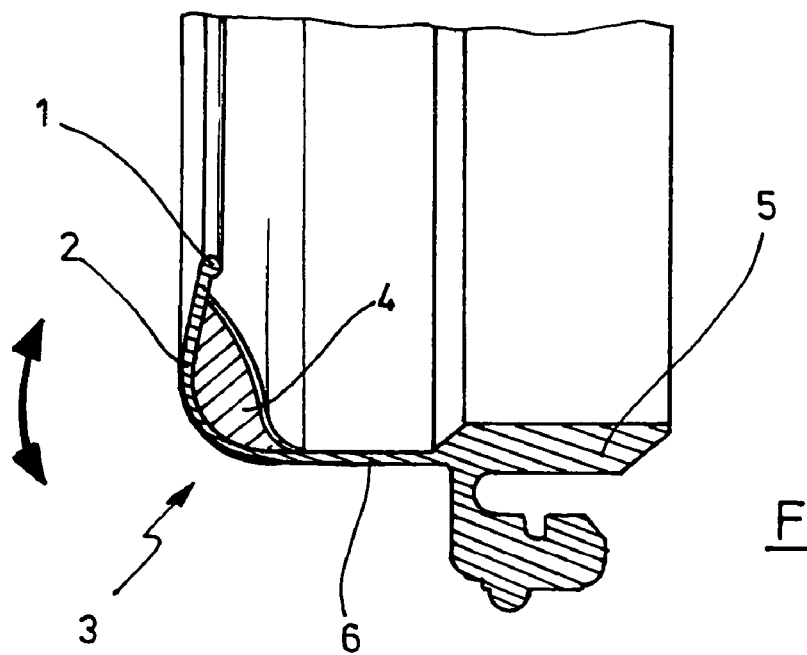
FIG. 2 shows an embodiment of the upper part of a mask with a cavity of limited extent.

FIG. 2 shows another preferred embodiment of the present invention, in which at least some regions of the upper part 3 of the mask have a cavity 4 that is limited to its inner corner region. This makes it possible to predetermine different properties of the upper part 3 of the mask and also to reduce costs.

Specifically, the contact lips 1 are provided with a pressure-producing underlay with a selected filler, while the wall region 6 remains free of any filler.

Figure 3:
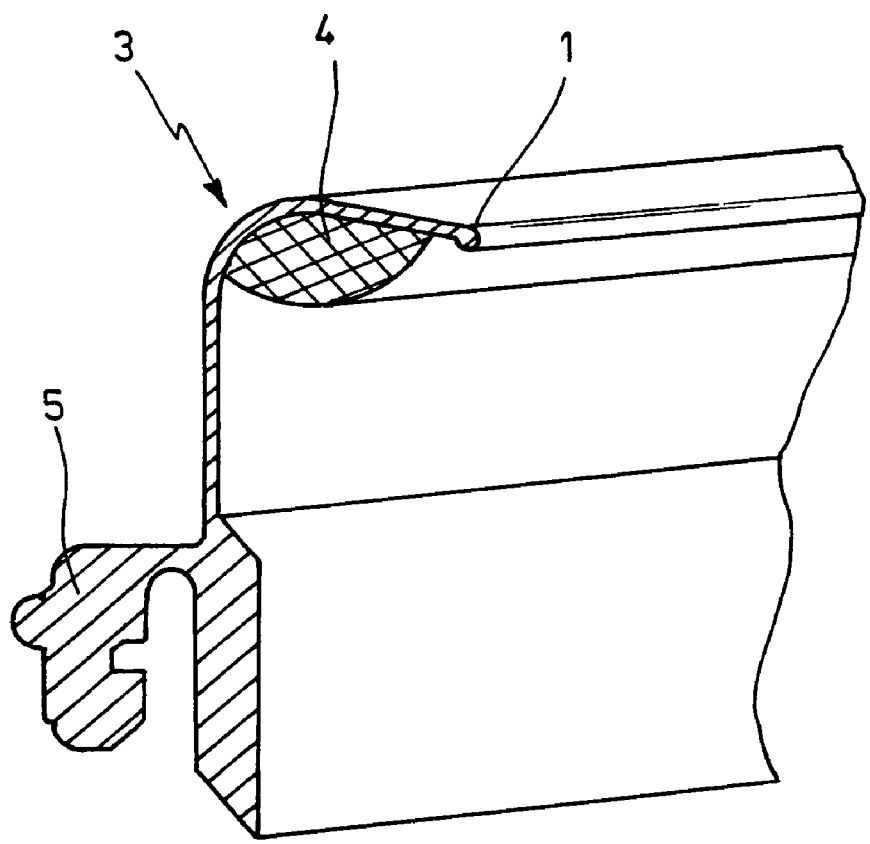
FIG. 3 shows an embodiment of the upper part of a mask with a cavity of limited extent in the inner corner region.

FIG. 3 shows a preferred embodiment with a cavity 4, which, as in FIG. 2, is limited to the corner region and whose shape is arched, especially concavely outward, so that the transitions to the filler-free parts of the wall of the upper part 3 of the mask are formed more abruptly, which makes it possible to predetermine other properties that are advantageous for some applications.

Figure 4:
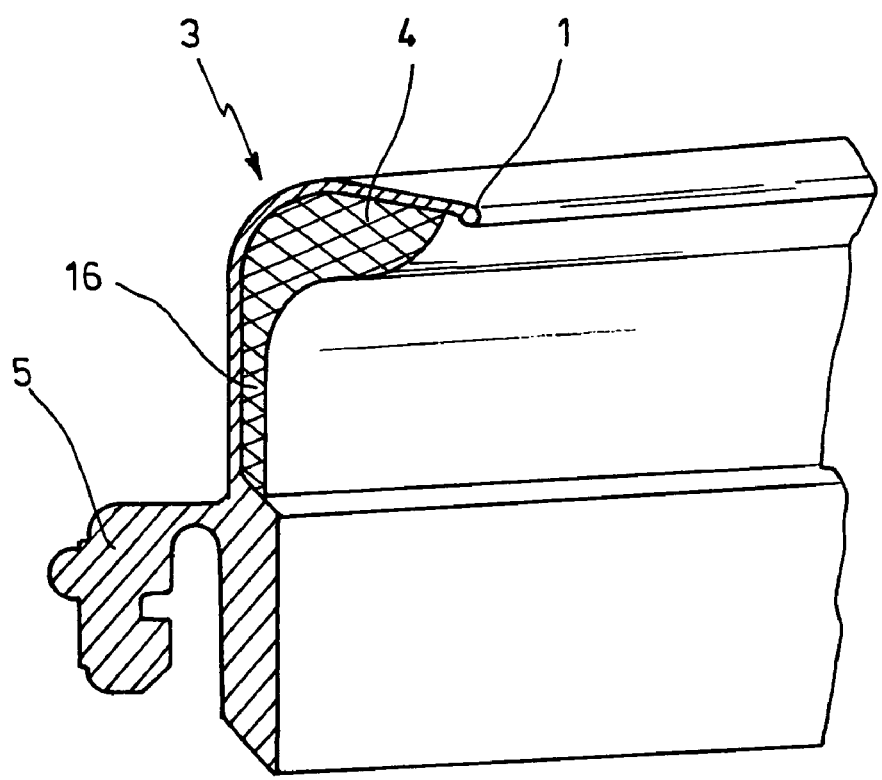
FIG. 4 shows an embodiment of the upper part of a mask with a cavity that extends over the entire inner surface of the upper part of the mask.

FIG. 4 shows another preferred embodiment of the invention, which has an additional elastic buffer zone 16 and for this reason is provided with a cavity 4 that extends over the additional elastic buffer zone 16. This makes it possible to select other advantageous elastic properties of the upper part of the mask, which can be determined either experimentally or mathematically.

By providing a thin filling of the cavity 4, for example, a soft buffer zone is realized. By filling the cavity 4 with relatively inflexible material, for example, with a gel with a hardness of greater than 15 Shore OO, the buffer zone 16 is given a protective function. The elastic buffer zone 16 can also be realized in such a way that at least certain regions of the filling have two different elastic properties.

Figure 5:
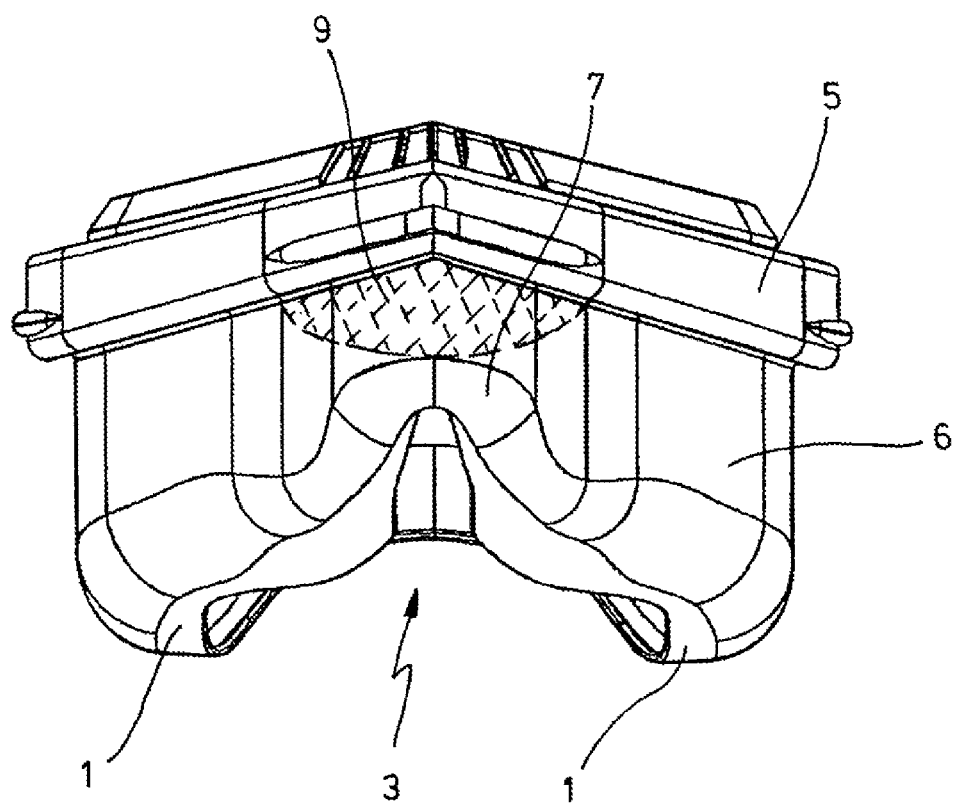
FIG. 5 is a top view of the upper part of a mask.

FIG. 5 shows a three-dimensional view of the upper part 3 of a mask that has contact lips 1, which are designed to surround the edge and are shaped to project inwardly into the upper part of the mask. The wall 6 of the upper part 3 of the mask serves to join it with the body of the mask (not shown) by means of mechanical snap-in elements, and it contains at least one cavity (not shown in the drawing) that is filled with a filler. The shaded region 9 in the region 7 of the upper part 3 of the mask that covers the bridge of the nose is constructed without a filler, for example, without gel. In another embodiment, no filler is provided in the entire region of the bridge of the nose.

Figure 6:
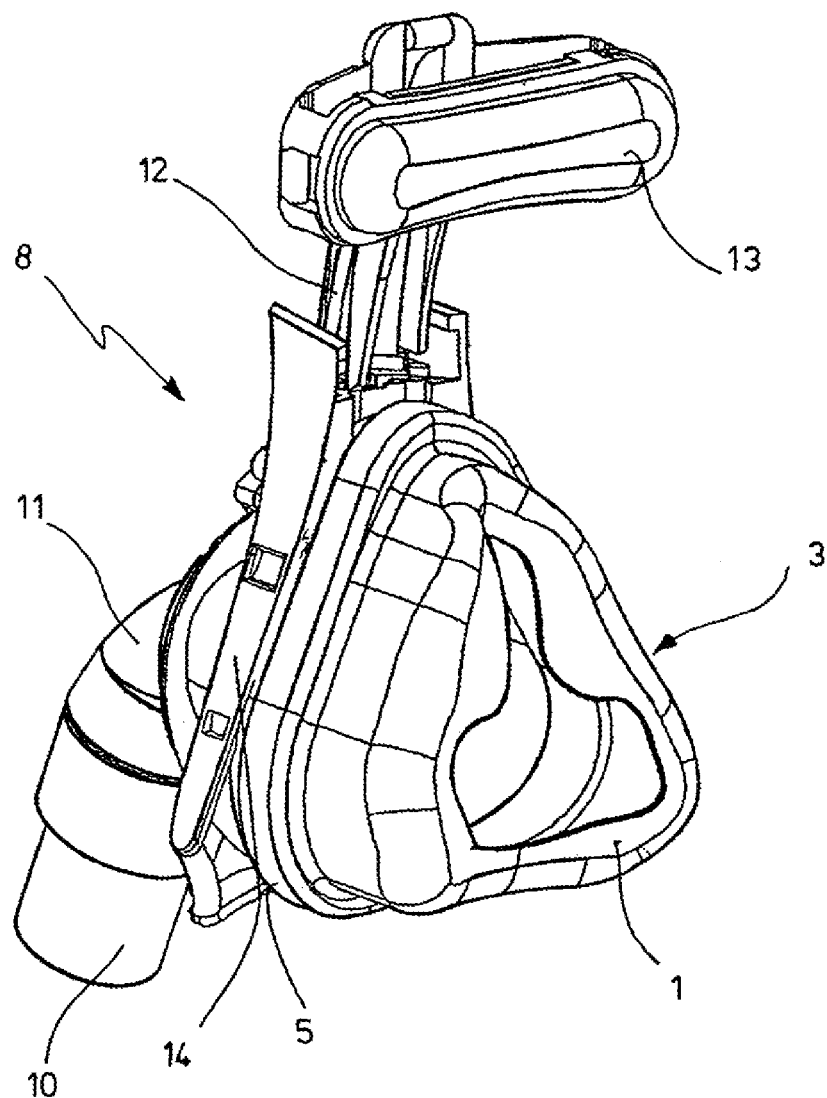
FIG. 6 is a general view of a ventilator mask.

FIG. 6 shows a design of the ventilator mask 8 with the upper part 3 of the mask. In its mask connection region 5, the upper part 3 of the mask is joined with the body of the mask 14 by snap-in mechanical elements, and otherwise the ventilator mask 8 has its familiar furnishings, such as a turn sleeve 10 for connecting an air-supply hose, which is rotatably connected with the body of the mask 14 by means of an elbow 11. A forehead pad 13 is slidably mounted on a mounting device 12 of the forehead support and provides additional support for the mask on the patient's forehead. The mask is fastened on the patient's head with straps (not shown).

Figure 7A:
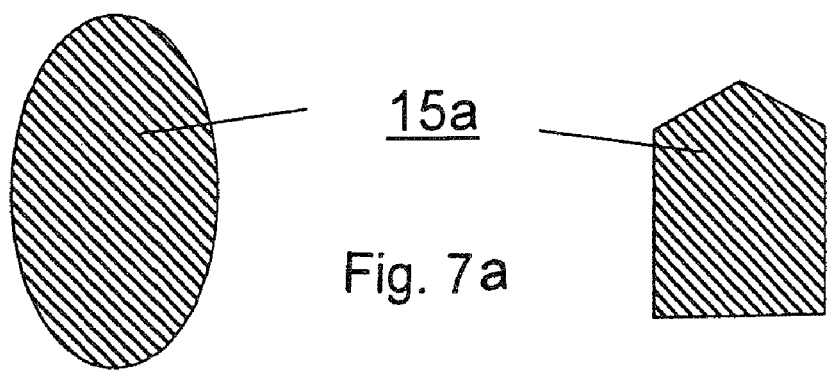
FIGS. 7(a)-7(c) show several cross sections through the cavity filled with filler 15.
Figure 7B:
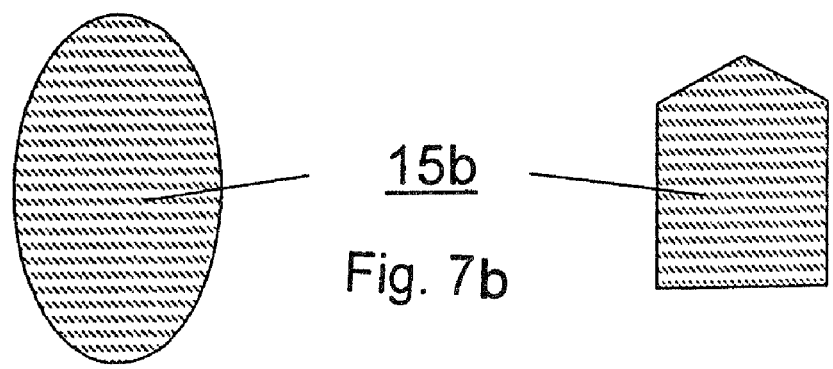
Figure 7C:
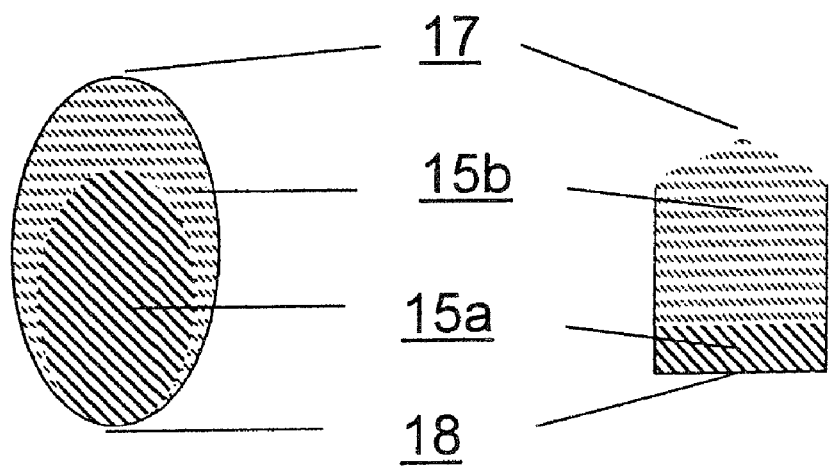

FIGS. 7(a) to 7(c) show cross sections through cavities that are filled with fillers 15. In FIGS. 7(a) and 7(b), the cavity is homogeneously filled with a filler. In FIG. 7(a), the filler 15a has greater hardness and lower elasticity than the filler in FIG. 7(b). In FIG. 7(b), the filler 15b has lower hardness and greater elasticity than the filler in FIG. 7(a).

In FIG. 7(c), the cavity 4 is inhomogeneously filled with filler 15a and 15b. The region 17 that is closer to the patient's face is filled with the softer filler 15b. The region 18 that is farther from the patient's face is filled with the harder filler 15b. Fillers with a hardness in the range of 5 Shore OOO to 15 Shore OO are preferably used as soft fillers, and fillers with a hardness value >15 Shore OO are preferably used as hard fillers.

FIGS. 7(a)-7(c) also show that the cavity filled with filler 15 can have different shapes.

The filler 15 of the invention makes it possible, within a very large range of designs, to provide the upper part 3 of the mask with a predetermined level of increased stability precisely in those regions in which this is required and to leave other regions of the upper part 3 of the mask with a thin wall thickness and/or a very soft material consistency.

The filling hole that has been repeatedly described can be designed as a hole in the conventional sense, which is closed again after the filler 15 has been applied. However, it is contemplated especially that the filler 15 be introduced with a flowable consistency by injection into the cavity 4. If this injection is carried out in a thick-walled region in a covering of the cavity 4, then after the injection device has been pulled out, the injection channel automatically closes due to the elastic properties of the material. This makes the production process much easier.

In accordance with the present specification, a preferred embodiment consists in forming the upper part 3 of the mask in the region 7 of the bridge of the nose so that it is flexible and soft in order to realize pleasant wearing comfort for the user. Therefore, the upper part 3 of the mask is formed in the region 7 of the bridge of the nose without additional use of the filler 15 or only with the use of a very soft filler 15b with a hardness value of, for example, <15 Shore OO.

Figure 8:
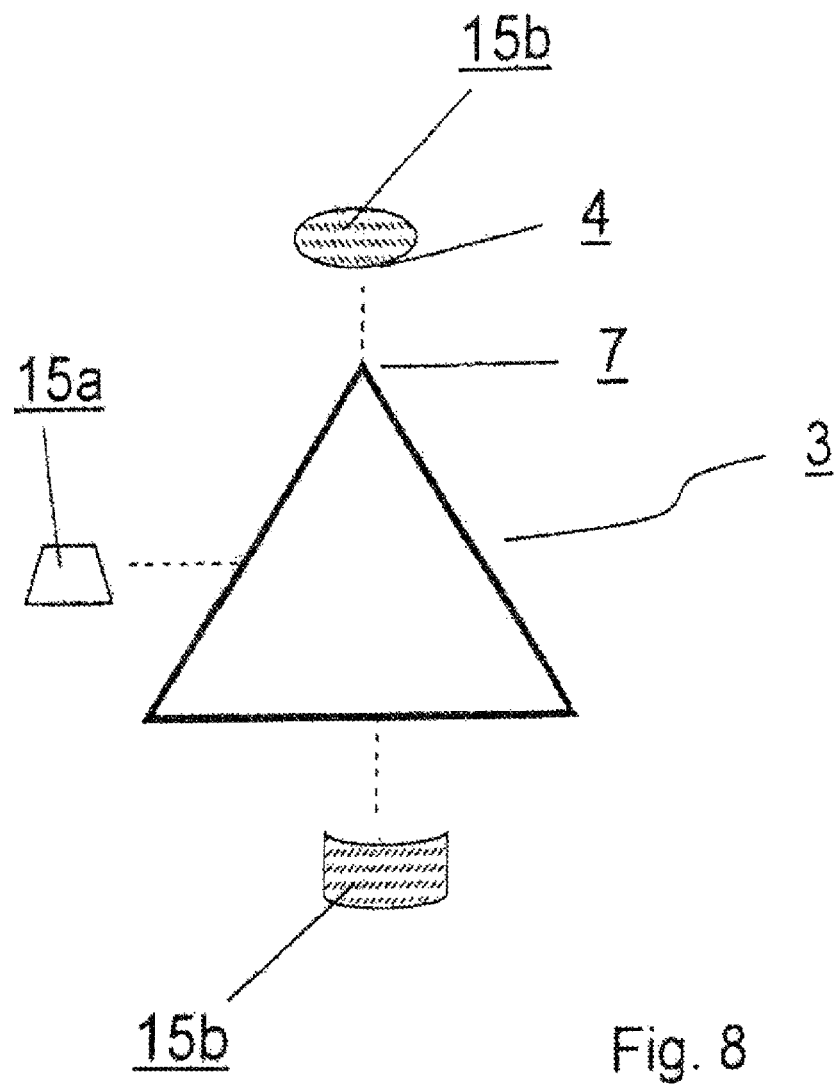
FIG. 8 is a schematic longitudinal sectional view through the upper part of the mask according to FIG. 6 and cross sections through the cavity 4 filled with fillings 15 in different places.

FIG. 8 shows a schematic longitudinal section through the essentially triangularly shaped upper part 3 of the mask according to FIG. 6 and cross sections through the filled cavity 4 in different places. A cross section through the filled cavity 4 in the region 7 of the bridge of the nose shows that the filling 15b is designed to be soft and elastic. The cavity is formed with a rounded elliptical shape in the region of the bridge of the nose. A cross section through the filled cavity 4 in the lateral area shows that the filling 15a is designed to be hard. The filled cavity 4 has an angular shape here, especially a trapezoidal shape. The cross section through the bottom of the upper part 3 shows that the filled cavity 4 also has a soft and elastic filling 15b.

In accordance with the invention, the shape of the filled cavity 4 varies along the periphery of the upper part of the mask, so that as a result of the locally different requirements on the upper part of the mask in each different region of the upper part of the mask, optimum sealing characteristics of the upper part of the mask can be realized.

In another embodiment, the walls 6 of the upper part of the mask can be selected with different material thicknesses, so that, on the one hand, the necessary stiffness is guaranteed and, on the other hand, contact with the skin that is as soft and tightly sealing as possible is guaranteed.

Especially in the region of the walls 6 of the upper part of the mask that rest against the face, the wall has a smaller material thickness than the regions of the walls of the upper part of the mask that do not rest against any part of the face. Smaller material thicknesses are preferably formed in the region of the walls of the upper part of the mask that rest on the bridge of the nose 7. It is especially preferred for the material thickness of the wall to be smaller in the region that rests on the bridge of the nose than in regions of the wall of the upper part of the mask that rest on other parts of the face. In this way, an optimum sealing function is realized with minimum application of pressure in the area of the sensitive bridge of the nose.

The cavity 4 is preferably inhomogeneously filled with filler 15 in such a way that regions of the filler that are close to the face are softer and more elastic than regions of the filler that are farther from the face. Two different goals are achieved in this way: on the one hand, a good protective function by the harder region farther from the patient's face and, on the other hand, a good sealing function and a high degree of flexibility in the region near the patient's face.

Figure 9:
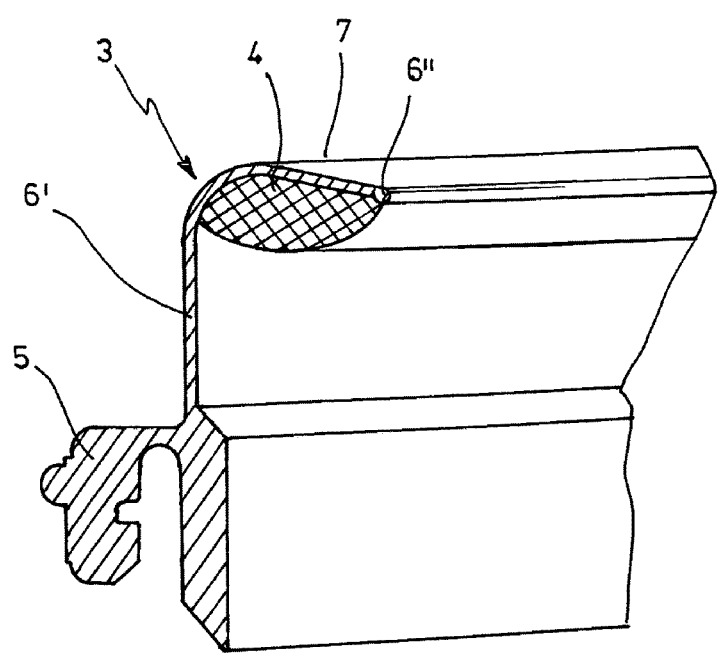
FIG. 9 shows an embodiment of the upper part 3 of a mask with different wall thicknesses in different regions.

FIG. 9 shows another preferred embodiment of the present invention, similar to those shown in FIGS. 2 and 3, in which the upper part 3 of the mask has a limited cavity 4, at least in certain regions. The wall 6' remains free of a filler. As a modification of the invention, the wall region is also designed with variable thickness. The wall region 6' that remains free of a filler is thinner and more flexible than the rest of the wall 6". The upper part of the mask in the region of the bridge of the nose 7 is preferably formed as illustrated in FIG. 9. Due to the thin wall 6', the upper part of the mask, especially in the region of the bridge of the nose, can adapt especially well to the geometry of the face. When the ventilator mask is worn and the ventilator is turned on, positive pressure prevails in the mask. The filled cavity then rests against and seals the face of the patient, while the soft wall 6', due to its flexibility, can be pressed outward as a function of the pressure, which is conducive to optimum adaptation to the particular facial contour.

In another preferred embodiment of the invention, the filled cavity is provided only in certain regions. Preferably, there is no filled cavity in the region of the bridge of the nose, or the cavity is not filled in the region of the bridge of the nose. In this case, a good seal and a high degree of flexibility of the upper part 3 of the mask in the region of the bridge of the nose is achieved by virtue of the fact that the wall 6' is thinner in this region. The wall 6' is preferably thinnest in the region of the bridge of the nose.

While specific embodiments of the invention have been described in detail to illustrate the inventive principles, it will be understood that the invention may be embodied otherwise without departing from such principles.

What is claimed is:

1. A ventilator mask comprising an upper part of an elastic material and a mask body, wherein the upper part of the mask is joined with the mask body of the ventilator mask by a mask connection region, wherein a wall of the upper part of the mask bounds at least in some regions of the wall a cavity which is filled with a filler at least in some regions of the cavity and the cavity is formed at least in some regions of the cavity along a periphery of the upper part of the mask, wherein, on a side that faces away from the mask body, the upper part has an inwardly formed, peripheral contact lip to form a soft and flexible contact zone, wherein the upper part of the mask has no cavity for the filler in a region that is adapted/configured to contact a bridge of a nose of a patient, where the cavity is inhomogeneously filled with filler in such a way that some regions of the filler that are adapted/configured to be close to a face of a patient are softer and more elastic than other regions of the filler, the contact lip being capable of providing an air seal in the region of the bridge of the nose.

2. The ventilator mask of claim 1, wherein an amount of filler and/or a filler property is different in at least two locations along the periphery of the upper part of the mask.

3. The ventilator mask of claim 1, wherein the amount of filler and/or a filler property is different in at least two locations along a cross-section of a surface the cavity.

4. The ventilator mask of claim 1, wherein a shape of the cavity and/or a size of the cavity differs in at least two locations along the periphery of the upper part of the mask.

5. The ventilator mask of claim 1, wherein a thickness of the wall differs in at least two locations along the periphery of the upper part of the mask.

6. The ventilator mask of claim 1, wherein properties of the filler are inhomogeneous, at least in some regions, along the periphery of the upper part of the mask.

7. The ventilator mask of claim 1, wherein properties of the wall are inhomogeneous in at least some regions thereof, along a cross section of the upper part of the mask.

8. The ventilator mask of claim 1, wherein properties of the filler are inhomogeneous, at least in certain regions along a cross section of the upper part of the mask.

9. The ventilator mask of claim 1, wherein the filler has different degrees of viscosity or hardness along a cross section of the upper part of the mask.

10. The ventilator mask of claim 1, wherein the cavity of the upper part of the mask has a variable depth along its cross section.

11. The ventilator mask of claim 1, wherein the filler is a gel.

12. The ventilator mask of claim 11, wherein the gel is a silicone gel or a polyurethane gel.

13. The ventilator mask of claim 1, wherein the filler is a foamed material.

14. The ventilator mask of claim 1, wherein the filler is one of a liquid, a gas mixture, and agarose.

15. The ventilator mask of claim 1, wherein the upper part of the mask has a wall of minimal thickness in a region of the bridge of the nose.

16. The ventilator mask of claim 1, wherein, at least in some regions, the filler has a hardness between 20 Shore OOO and 5 Shore OO.

17. The ventilator mask of claim 1, wherein, at least in some regions, the filler has a hardness between 10 Shore OO and 20 Shore OO.

18. The ventilator mask of claim 1, wherein a thickness or depth of the filler varies along a cross section of the upper part of the mask.

19. A method of producing an upper part of a ventilator mask, wherein the method comprises forming the upper part of the mask of a flexible material, providing the upper part with a cavity at least in some regions thereof, and with at least one hole through which filler can be introduced into the cavity, using a gel as the filler, and inhomogeneously filling the cavity with the filler so that some regions of filler in the upper part of the mask are softer and more elastic than other regions in the upper part of the mask.

20. The method of claim 19, further comprising inserting the filler in the cavity in the form of a sealed body.

21. A method for producing an upper part of a ventilator mask, wherein the method comprises producing a shaped rim by spraying filler from a nozzle onto a wall of the upper part of the mask, the applied amount of filler being varied to achieve a desired shaping of the rim, and the filler only being introduced on an inner surface or an outer surface of walls of the upper part of the mask.

22. The method of claim 21, wherein a gel or a foamed material is used as the applied filler.

23. The method of claim 21, wherein the rim sprayed onto the wall is provided with a protective layer.

* * * * *